(12) United States Patent
Partin

(10) Patent No.: US 8,048,134 B2
(45) Date of Patent: Nov. 1, 2011

(54) ACTIVE COMPRESSION TO FACILITATE HEALING OF BONES

(75) Inventor: Jason Ian Partin, Encinitas, CA (US)

(73) Assignee: Andrew K. Palmer, Eastham, MA (US)

( * ) Notice: Subject to any disclaimer, the term of this patent is extended or adjusted under 35 U.S.C. 154(b) by 689 days.

(21) Appl. No.: 11/697,655

(22) Filed: Apr. 6, 2007

(65) Prior Publication Data

US 2007/0270855 A1 Nov. 22, 2007

Related U.S. Application Data

(60) Provisional application No. 60/790,178, filed on Apr. 6, 2006, provisional application No. 60/810,340, filed on Jun. 2, 2006.

(51) Int. Cl.
*A61B 17/86* (2006.01)

(52) U.S. Cl. ......... 606/320; 606/301; 606/314; 606/315

(58) Field of Classification Search .......... 606/300–302, 606/306, 309, 314–316, 319–321, 303–305, 606/307, 308, 310–313, 317, 318; 411/341, 411/342, 392, 907, 916
See application file for complete search history.

(56) References Cited

U.S. PATENT DOCUMENTS

| | | | |
|---|---|---|---|
| 4,947,502 A | 8/1990 | Engelhardt | |
| 4,959,064 A | 9/1990 | Engelhardt | |
| 5,057,111 A | 10/1991 | Park | |
| 5,102,276 A | 4/1992 | Gourd | |
| 5,415,660 A | 5/1995 | Campbell et al. | |
| 6,296,645 B1 | 10/2001 | Hover et al. | |
| 6,443,954 B1 | 9/2002 | Bramlet et al. | |
| 6,458,134 B1 | 10/2002 | Songer et al. | |
| 6,517,543 B1 | 2/2003 | Berrevoets et al. | |
| 6,656,184 B1 * | 12/2003 | White et al. | 606/318 |
| 6,736,819 B2 | 5/2004 | Tipirneni | |
| 6,755,862 B2 | 6/2004 | Keynan | |
| 6,761,719 B2 | 7/2004 | Justis et al. | |
| 6,808,527 B2 | 10/2004 | Lower et al. | |
| 2001/0007074 A1 | 7/2001 | Strobel et al. | |

(Continued)

FOREIGN PATENT DOCUMENTS

DE 28 21 678 A1 11/1979

(Continued)

OTHER PUBLICATIONS

The International Search Report from PCT International Application No. PCT/US2007/008535 filed on Apr. 6, 2007.

*Primary Examiner* — Thomas C. Barrett
*Assistant Examiner* — Michael T Schaper
(74) *Attorney, Agent, or Firm* — Heslin Rothenberg Farley & Mesiti P.C.

(57) ABSTRACT

A bone fixation device includes one or more springs and one or more spacers disposed between two orthopedic structures. The orthopedic structures may comprise screws, rods, plates, or any other orthopedic devices configured to engage bone. The spacer may be absorbable or removable, and may serve to constrain the spring in a compressed or stretched state so that, upon absorption or removal of the spacer, the spring may apply tension or compression to surrounding bone. The device may thereby facilitate healing or bone or remodeling of soft tissues.

33 Claims, 13 Drawing Sheets

U.S. PATENT DOCUMENTS

| | | |
|---|---|---|
| 2003/0158555 A1* | 8/2003 | Sanders et al. .................. 606/73 |
| 2004/0153156 A1* | 8/2004 | Cohen et al. ............... 623/17.13 |
| 2004/0172030 A1 | 9/2004 | Tipirrneni |
| 2005/0113928 A1* | 5/2005 | Cragg et al. ............... 623/17.16 |
| 2005/0288672 A1 | 12/2005 | Ferree |
| 2006/0036240 A1 | 2/2006 | Colleran et al. |
| 2006/0264954 A1* | 11/2006 | Sweeney et al. ................ 606/73 |
| 2007/0162026 A1 | 7/2007 | Tipirneni et al. |
| 2007/0260248 A1 | 11/2007 | Tipirneni |
| 2008/0147127 A1 | 6/2008 | Tipirneni et al. |

FOREIGN PATENT DOCUMENTS

| | | |
|---|---|---|
| WO | WO 2005/044117 A2 | 5/2005 |

* cited by examiner

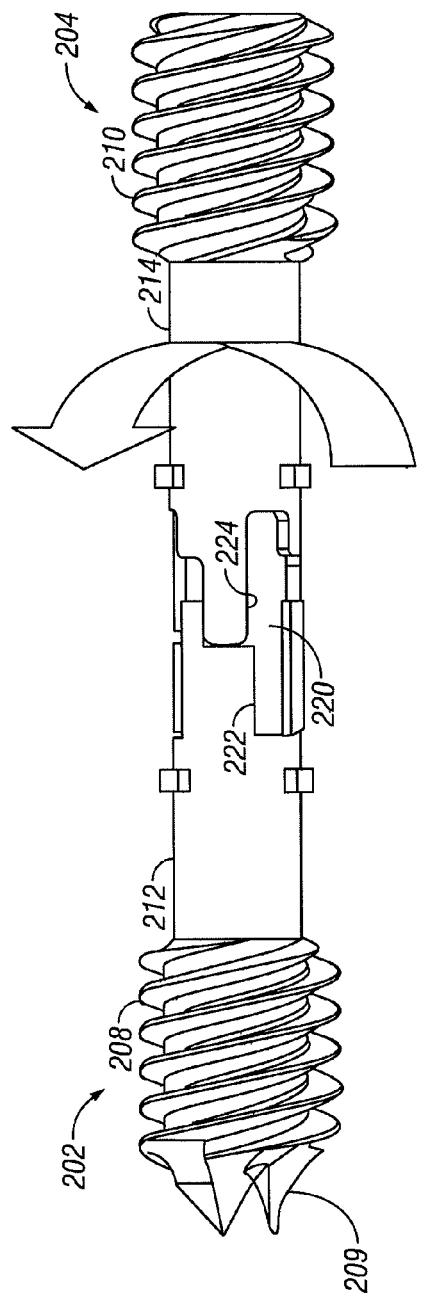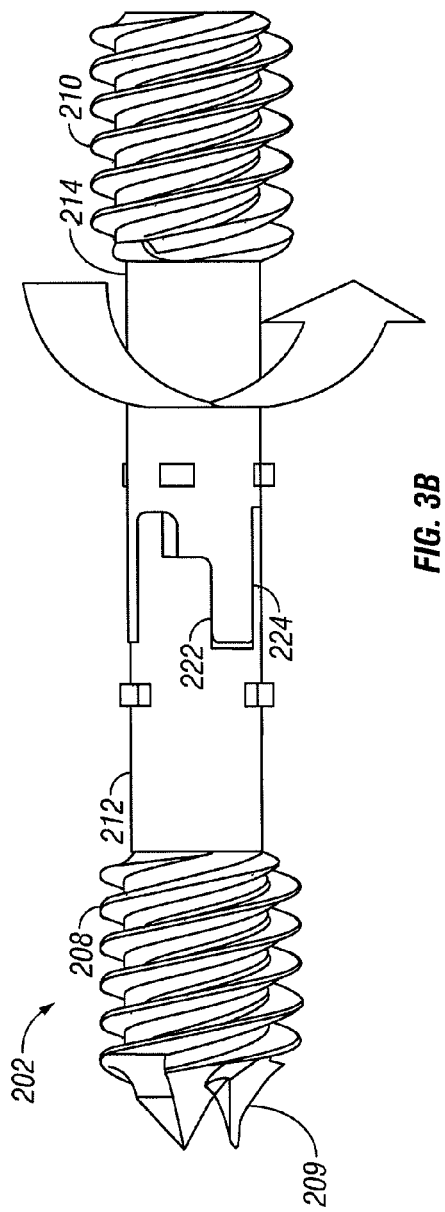
FIG. 3A
FIG. 3B

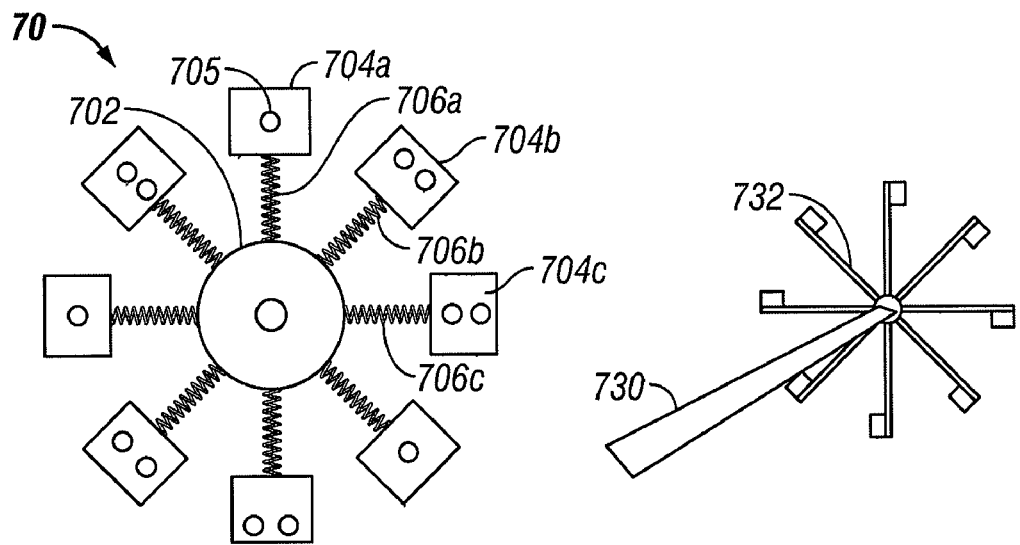
FIG. 9A  FIG. 9B
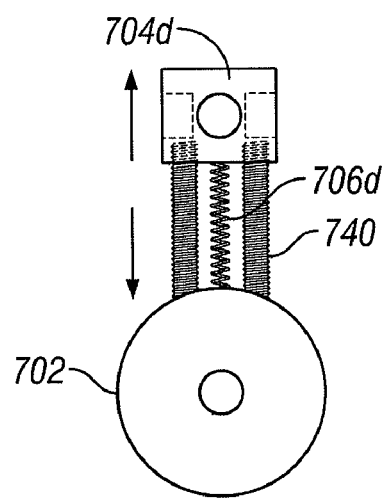
FIG. 10

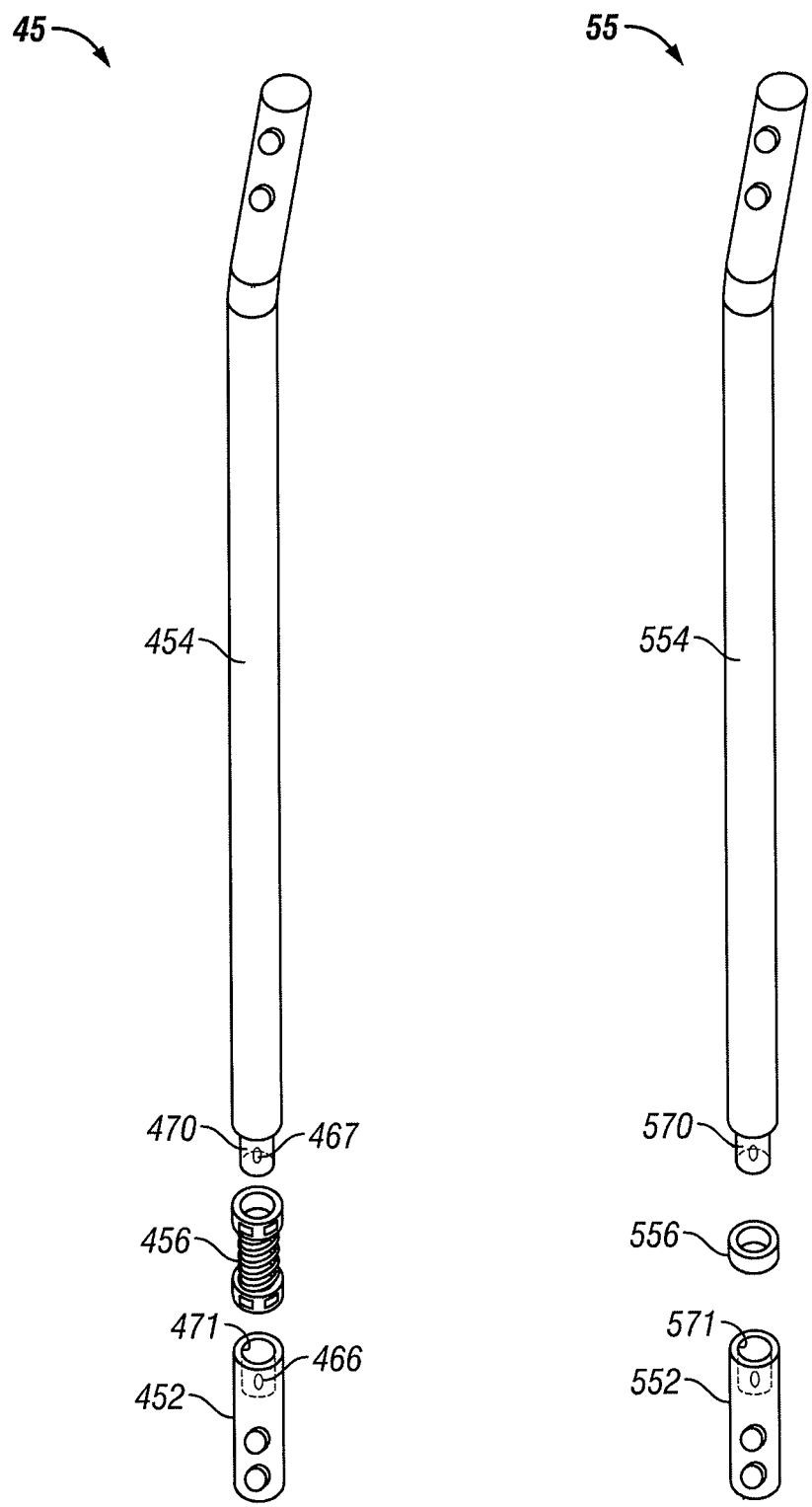
*FIG. 14A*          *FIG. 14B*

ACTIVE COMPRESSION TO FACILITATE HEALING OF BONES

CROSS-REFERENCE TO RELATED APPLICATIONS

This application claims priority to U.S. Provisional Application Nos. 60/810,340, entitled "Methods and Devices for Applying Compression with Orthopedic Plates, Screws, Rods, and Nails," filed Jun. 2, 2006; and 60/790,178, also entitled "Methods and Devices for Applying Compression with Orthopedic Plates, Screws, Rods, and Nails," filed Apr. 6, 2006. The entire disclosures of the above-referenced provisional applications are herein incorporated by reference in their entirety.

BACKGROUND OF THE INVENTION

1. Field of the Invention

This application relates generally to the field of orthopedic devices, and, more particularly, to orthopedic devices used in fusing bone together.

2. Description of the Related Art

Arthritis or damage to joints is commonly treated with a fusion to eliminate motion. Fractures and osteotomies are often treated with internal plating to align bones and facilitate healing. Because bone grows in response to mechanical loading, many physicians attempt to increase the strength of new bone or accelerate healing by applying compression across a fracture or fusion site. Physicians often create multiple surgical openings to apply plates and screws in an attempt to provide compression in multiple directions. In some cases a second surgery is required to remove one or more of these constraints to allow load transfer across the healing bone. Additionally, spinal segments are often compressed or distracted before tightening screws or plates to restore alignment to soft tissues. In all cases the compression or adjustment is applied at the time of surgery.

SUMMARY OF THE INVENTION

Aspects of the present invention include a bone fixation device comprising at least two orthopedic structures, a spring, and a spacer. The spring is disposed between the orthopedic structures. The spacer is configured to hold the orthopedic structures apart against a force applied between the structures. The applied force is transmitted to the spacer through contact between the spacer and the orthopedic structures.

Other aspects of the present invention include a method of attaching bone to bone. The method includes the steps of inserting a first orthopedic structure into a first piece of bone and inserting a second orthopedic structure into a second piece of bone. The method further includes manually inducing a force between the first and second orthopedic structures after the orthopedic structures have been inserted.

Still other aspects include a kit comprising a bone fixation device and at least one spacer. The bone fixation device comprises two orthopedic structures configured to engage bone. The spacer is configured to reversibly couple to the device and to contact the orthopedic structures to hold them apart from each other.

Still further aspects include an intramedullary nail comprising a proximal member, a distal member, and a spacer. The proximal member is configured to attach to bone within a bone marrow canal. The distal member is also configured to attach to bone within a bone marrow canal. The spacer is positioned between the proximal and distal members and is configured to resist axial movement of the proximal and distal members toward each other.

BRIEF DESCRIPTION OF THE DRAWINGS

FIGS. 3A and 3B are side views of the compression device of FIG. 1 (with the spring member not shown) illustrating the interengaging action of the two orthopedic structures of the device.

FIG. 9A shows a top plan view of a multi-fragment compression device according to still another embodiment.

FIG. 9B is a perspective representation of a spacer comprising a restraining instrument adapted for use with the compression device of FIG. 9A.

FIG. 10 is a top plan view of a portion of a multi-fragment compression device according to another embodiment.

FIG. 14A is an exploded view of an intramedullary compression device using a compressible spring member according to an embodiment.

FIG. 14B is an exploded view of an intramedullary compression device using an absorbable spacer according to an embodiment.

DETAILED DESCRIPTION OF CERTAIN INVENTIVE ASPECTS

Figure 1:
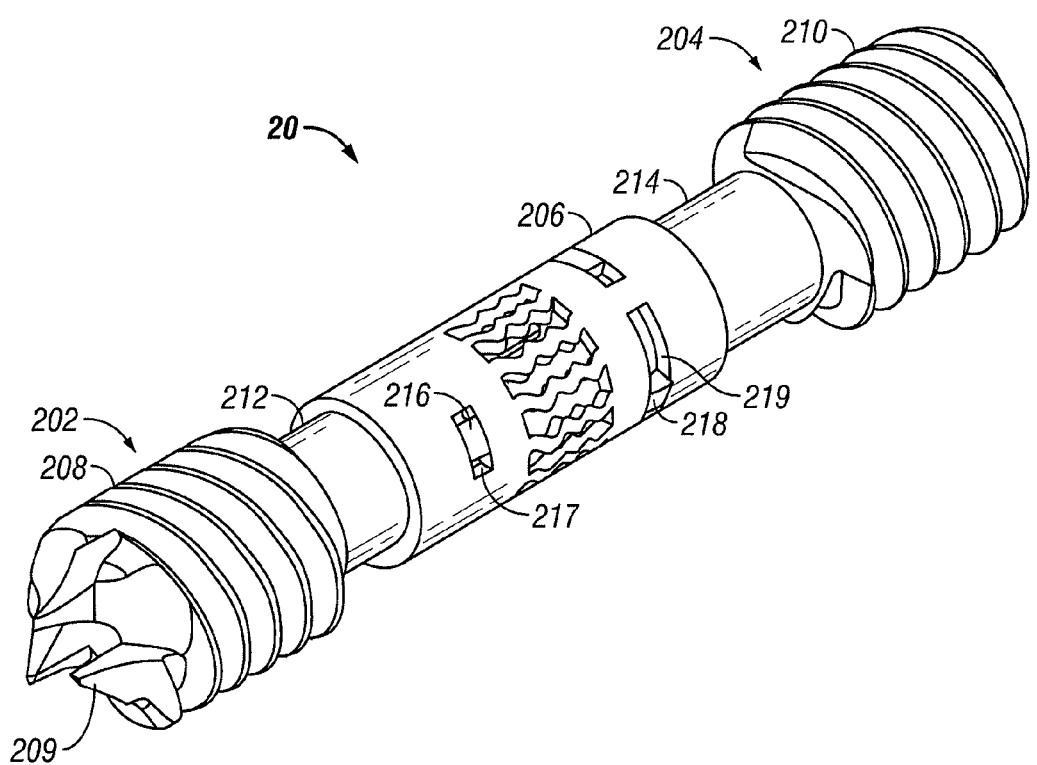
FIG. 1 is a perspective view of a compression device according to an embodiment of the invention.

The features, aspects and advantages of the present invention will now be described with reference to the drawings of several embodiments, which are intended to be within the scope of the invention herein disclosed. These and other embodiments will become readily apparent to those skilled in the art from the following detailed description of the embodiments having reference to the attached figures, the invention not being limited to any particular embodiment(s) disclosed.

As mentioned in the Background section, bone grows (and therefore heals) in response to compressive loading. Conventional fusion techniques include applying compression across a fusion site using a screw or plate at the time of surgery. However, compressive forces applied during surgery can quickly return to neutral after surgery, especially as bone begins to heal or soft tissue begins to remodel. Additional surgeries are often required to apply further compression by removing one or more constraints. Alternatively, absorbable materials can be used to gradually transfer loads from an implanted orthopedic device to bone. These materials, however, are often too weak to support daily activities prior to bone healing.

Nitinol and other shape-memory materials can be used to apply compression to fusion sites after surgery is completed. These materials have not been widely used, however, due at least in part to their high manufacturing costs. These materials are also temperature sensitive and are manufactured to transition and apply forces at or near body temperature. Thus, they can be sensitive to varying temperatures in a surgical environment, adding complexity and expense to surgical procedures.

Thus, various embodiments of the invention advantageously provide cost-effective devices and methods for applying compression to bone fusion sites both during and after surgery. Other embodiments of the invention advantageously provide cost-effective devices and methods for applying tension to bones to facilitate lengthening or remodeling or alignment of soft tissues.

Some embodiments of the invention provide "active compression," that is, they provide continuous compressive forces to bone that adjust in vivo as bone heals. Similarly, some embodiments of the invention provide tension forces to bone that adjust in vivo as soft tissue remodels. Various embodiments thus promote post-operational growth and healing of bones, as well as healing and remodeling of soft tissue, without the need for additional surgical procedures to adjust or remove constraints. Other embodiments further provide devices and methods for compressing bone in multiple directions using one system, thereby eliminating the need for multiple surgical approaches to handle a complex fracture or fusion site.

In some embodiments, the structures described herein advantageously offer sufficient initial strength to support normal daily activities while the bone heals. Some embodiments are also capable of applying controlled amounts of compression (or tension) at desired times throughout the healing process. Some embodiments also provide for bending resistance and/or torsional resistance across a bone fusion device where such resistance is desirable. Embodiments of the invention further allow for use of non-absorbable (intra-operatively adjustable and/or removable) spacers to hold a device in a stressed state or a neutral state for a desired amount of time, completely independent of temperature or other variables. Various embodiments thus allow for application-specific, patient-specific, and/or time-controlled application of compression or tension both during and after surgery.

Conventional threaded bone fusion systems achieve compression using differing leading and trailing threads. Because compression begins to occur as soon as the trailing thread engages the bone, practitioners must precisely size the system by measuring the exact distance from a fracture site to the edge of the bone. Embodiments of the invention, however, may include leading and trailing sections having identical threads, and are adjustable in both the backwards and forwards directions without any loss of compression. This allows for more robust sizing of these and other embodiments. This further allows practitioners to use standard driver or drill instrument with variously-sized embodiments. Embodiments including threaded orthopedic devices also offer the advantage of limiting the possibility of over-compression and consequent stripping of bone, problems that can result from conventional bone fusion devices.

Conventional bone fusion devices employing absorbable materials apply shear or bending stress to the absorbable materials. Some embodiments of the invention, however, load an absorbable spacer in compression. Thus, absorbable spacers are subjected to primarily normal stresses, requiring only a small amount of absorbable material to achieve the desired results.

Some embodiments of the invention generally include two or more orthopedic devices joined together by a spring and held apart by a spacer. As used herein, the term "orthopedic structure" or "orthopedic device" can refer to any device configured to engage bone, such as a plate, screw, rod, or nail, or portions thereof (e.g., the threading of a screw or the head of a screw or nail). An orthopedic device can comprise any biocompatible material, including common, cost-effective materials such as Titanium, $Ti_6AL_4V$, Stainless Steel, Cobalt Chromium, Pyrolytic Carbon, or PEEK.

As used herein, the term "spring" can refer to any device that applies a reversible force in response to compressive or tensile loading. A spring may include one or more coiled, bent, or angled portions. A spring may comprise one or more elastic portions, as well as one or more inelastic portions. A spring can be curved so as to move bone or soft tissue in a desired direction instead of, or in addition to, applying compression or distraction. A spring can comprise any metallic or polymer material. Alternatively, a spring can comprise Nitinol or some other super elastic or shape memory material. A spring can further comprise a material which is activated by temperature upon removal of a constraint or spacer. A spring can be configured to attach to an orthopedic device with a press fit, mechanical interlock, weld, bond, fastener, or other coupling. The force applied by a spring can be any suitable amount. Non-limiting examples include between about 0.5 pounds and about 30 pounds, between about 1 pound and about 20 pounds, or between about 3 pounds and about 14 pounds.

The term "spacer," as used herein, can refer to any device, instrument, or mechanism configured to hold two orthopedic devices together or apart. A spacer can also refer to any device, instrument, or mechanism configured to hold a spring in a neutral, compressed, stretched, or shifted state. For example, a spacer can comprise a removable metal or polymer insert, or an absorbable material, disposed between two orthopedic devices or between two ends of a spring. A spacer can also be a deformable spacer which is less rigid than an orthopedic structure so that the spacer acts as a dampener or shock absorber between orthopedic structures. Alternatively, a spacer can comprise a tool or other instrument configured to engage two orthopedic devices (or two ends of a spring) and hold them apart or pull them together. Compression or tension can occur when the restraints are released (either by releasing the elastic properties of the spring or allowing contraction or expansion as the spring changes temperature). A spacer can include markers indicating the amount of compression or distraction applied by a given configuration. In some embodiments, the spacer, or separate portions thereof, may be integral with one or more orthopedic structures.

Figure 2:
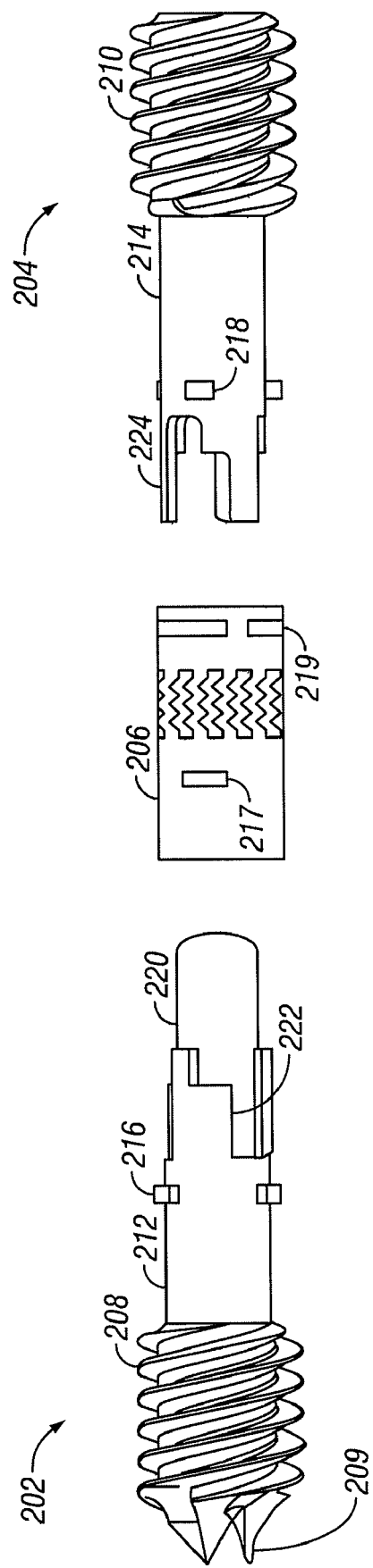
FIG. 2 is an exploded view of the device of FIG. 1.

With reference now to FIGS. 1-2, a bone fixation device may include a compression screw 20 that includes a leading orthopedic structure 202 and a trailing orthopedic structure 204, with a spring 206 disposed between the two. The leading orthopedic structure 202 may include a threaded portion 208 for engaging bone. In some embodiments, the leading orthopedic structure 208 also includes drilling teeth elements 209 or some other pointed tip structure for removing bone material as the screw 20 is driven into bone. The leading orthopedic structure 202 may further include an unthreaded portion 212.

The trailing orthopedic structure 204 may also include a threaded portion 210 for engaging bone, as well as an unthreaded portion 214. As will be discussed in further detail below in connection with FIG. 3, the unthreaded portions 212, 214 may include structures that together form a spacer to selectively hold the leading 202 and trailing 204 orthopedic structures apart against the compressive force of the spring 206. The spacer in conjunction with the spring 206 allows for selective advancement and retreat of portions of the device 20.

As depicted in FIG. 2, the unthreaded portion 212 of the leading orthopedic structure 202 may comprise one or more protrusions 216 configured to closely engage with slots 217 located at the leading section of the spring 206. The unthreaded portion 214 of the trailing orthopedic structure 204 may comprise one or more protrusions 218 configured to rotatably engage with slots 219 located at the trailing section of the spring 206. Alternatively, the spring 206 can be press fit, welded, or otherwise retained or secured to the unthreaded portions 212, 214 of the leading and/or trailing orthopedic structures 202, 204.

The unthreaded portions 212, 214 may each have a diameter smaller than that of the screw portions 208, 210, and substantially equivalent to the internal diameter of the spring 206. The unthreaded portion 212 of the leading orthopedic structure 202 may additionally comprise a core 220 or other protrusion configured to engage with an aperture or other structure on the trailing orthopedic structure 204. The core 220 of the leading orthopedic structure 202 may have a smaller diameter than that of the unthreaded portion 212. The trailing orthopedic structure 204 may be hollowed out to receive the core 220 of the leading orthopedic structure 202. By this configuration, the leading and trailing orthopedic structures 202, 204 cooperate to resist bending in the device 20 while allowing the spring 206 to be stretched or compressed in an axial direction. In applications in which torsional resistance is also desired, the core 220 of the leading orthopedic structure 202 and matching aperture in the trailing orthopedic structure 204 may include elliptical or other non-circular cross sections. Alternative embodiments may include other configurations designed to resist bending and/or torsion in the device, such as tongue and groove, dovetail, keyed, angled, sliding, or other configurations. In embodiments in which the spring itself provides sufficient bending resistance, additional bending resistance members may not be required.

With reference to FIG. 2, the leading and trailing orthopedic structures 202, 204 may also include interengaging structures 222, 224, respectively, which together may form an adjustable spacer configured to adjustably maintain spacing between the leading and trailing orthopedic structures 202, 204. In the illustrated embodiment, the interengaging structures 222 and 224 are configured to maintain spacing of the leading and trailing orthopedic structures 202, 204 so that their respective threaded portions 208, 210 have the same thread alignment and function as a continuous screw. The screw 20 or any portion of it may further be cannulated to facilitate insertion of drivers or guide wires.

As illustrated in FIG. 3A, the structures 222, 224 can cooperate to selectively restrict and transmit axial rotation and/or axial translation between the leading 202 and trailing 204 orthopedic structures of the screw 20. Specifically, the end surface of structure 224 contacts an end surface of structure 222 to hold orthopedic structures 202 and 204 apart (e.g., against a compressive force applied by spring 206). In addition, a side surface of structure 224 contacts a side surface of structure 222 to transmit clockwise axial rotation from the trailing orthopedic structure 204 to the leading orthopedic structure 202, thereby allowing the screw 20 to be driven into bone as a continuous screw using a driving tool coupled to the trailing orthopedic structure 204.

As illustrated in FIG. 3B, once the screw is fully inserted, the trailing orthopedic structure 204 may be rotated counterclockwise relative to the leading orthopedic structure 204 such that the structure 224 no longer contacts the same end surface of structure 222, thereby permitting axial translation of the leading 202 and trailing 204 orthopedic structures (e.g., in response to a compressive force applied by spring 206). The rotatable engagement between protrusions 218 on the trailing orthopedic structure with slots 219 in the spring (see FIGS. 1 and 2) allow for this relative counterclockwise rotation. In addition, one or more side surfaces of the structure 224 contacts one or more side surfaces of the structure 222 to transmit counterclockwise or both clockwise and counterclockwise axial rotation from the trailing orthopedic structure 204 to the leading orthopedic structure. Thus, in this configuration, the screw can be further advanced or withdrawn using a driving tool coupled to the trailing orthopedic structure 204.

In embodiments where the spring 206 is a tension spring, the spacer comprising structures 222 and 224 may hold the leading 202 and trailing 204 orthopedic structures apart under the compressive force of the stressed spring 206 when in the configuration of FIG. 3A. After insertion of the screw 20, the configuration may be changed to that of FIG. 3B to allow the tension spring 206 to urge the leading 202 and trailing 204 structures together. In some embodiments, these screws 20 may be used to attach various other orthopedic structures to bone without losing tight engagement with the bone over time. In other embodiments, these screws 20 may be used across a bone fracture such that the leading orthopedic structure 202 engages bone on one side of the fracture while the trailing orthopedic structure 204 engages bone on the other side of the fracture. In this configuration, the screw 20 supplies a compressive to the fracture through tension spring 206.

In embodiments where the spring 206 is a compression spring, the spacer comprising structures 222 and 224 may provide a rigid relationship between the structures so that the screw 20 can be easily inserted into bone with the spring 206 in a relaxed state when the screw 20 is in the configuration of FIG. 3A. After screw 20 insertion, the configuration may be changed to that of FIG. 3B so that the compression spring 206 may provide resistance to forces applied by the body to the screw 20.

Some embodiments include surgical methods using the screw 20 described above. In one such embodiment, the surgeon positions bone pieces close together that are desired to be fused. Next one or more screws 20 described above are inserted into the bone across the bone fracture(s). In some embodiments, holes may be predrilled prior to screw insertion. In other embodiments, screws are inserted directly into un-drilled bone. After driving the screw into the bone across the fracture(s), the trailing orthopedic structure 204 is rotated counterclockwise to allow the spring 206 to provide a compressive force between the bone fragments. The screw 20 may then be further turned clockwise or counterclockwise to position it at the desired depth. After sufficient bone healing, the screw may be optionally removed.

Figure 4A:
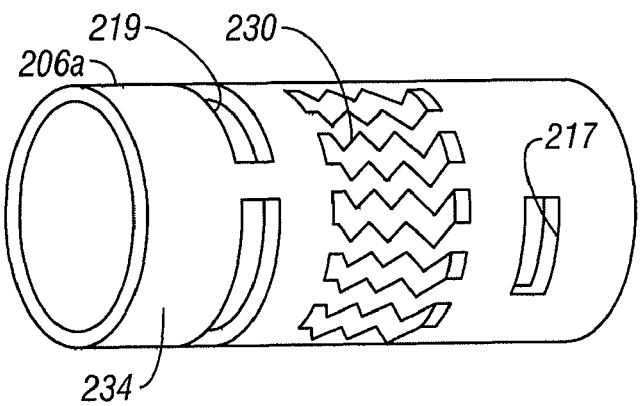
FIG. 4A is a perspective view of the spring of the compression device of FIG. 1.
Figure 4B:
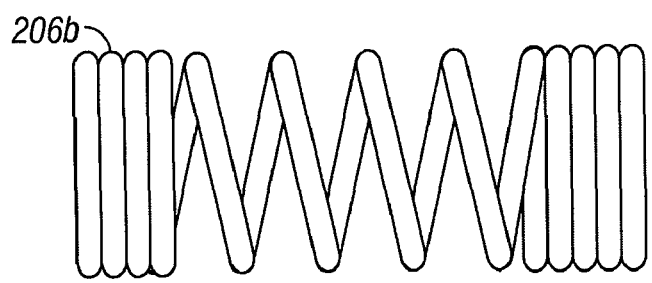
FIGS. 4B-4C are side views of springs according to alternative embodiments.
Figure 4C:
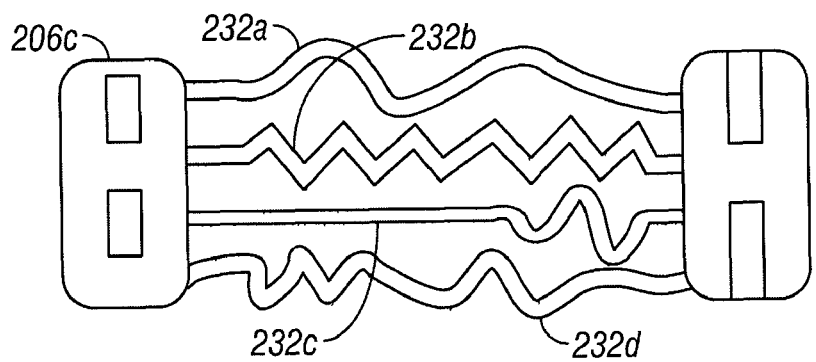

With reference now to FIGS. 4A-C, various designs of springs according to alternative embodiments are illustrated. FIG. 4A shows a spring 206(*a*) which may comprise a temperature transition, super elastic, or elastic member provided with at least one bending angle 230 or radius of curvature to facilitate elongation. The spring 206(*a*) may be cut from a single tube of material, or can be formed from one or more non-continuous tubes or portions to facilitate placement on an orthopedic device. Likewise, the spring 206(*a*) may optionally be provided with one or more collars 234 having slots or holes 217, 219 to facilitate placement on an orthopedic device. As shown in FIG. 4B, a spring 206(*b*) may also comprise a coil spring made from one or more elastic materials, such as surgical steel wire, for example. As discussed earlier, these spring designs may be tension or compression springs, depending on the desired application. In these embodiments and others, the spring may approximate the linear spring relationship $F=kx$, where F is the force applied, k is the spring constant, and x is the amount of displacement. In other embodiments the spring is designed with variable thicknesses or spring elements of different thicknesses so that the combined force is approximately constant. FIG. 4C, for example, shows a spring 206(*c*) according to an alternative embodiment, the spring 206(*c*) comprising a plurality of compressive portions 232(*a*), 232(*b*), 232(*c*), and 232(*d*) having varied curvatures and/or bends along their lengths in order to provide a relatively constant compressive force even as loading changes. The compressive portions 232 may be provided with staggered curvatures in order to increase resistance to bending between orthopedic devices. The compressive portions 232 may additionally be provided with notches or cuts, or otherwise configured to provide different spring constant values in the same spring. If the force applied through each portion 232 is $F=kx$, the total force across the device would be $F_{total}=(k_1 x_1)+(k_2 x_2)+$etc.

Although the illustrated springs generally maintain the same cross-sectional profile in both tension and compression, embodiments of the invention may include a spring having a wider or larger cross-sectional profile in compression than in its relaxed state, including in some embodiments a spring having a cross-sectional profile larger than an insertion hole in bone. Similarly, embodiments may include a spring having a narrower or smaller cross-sectional profile in tension than in its relaxed state.

Figure 5A:
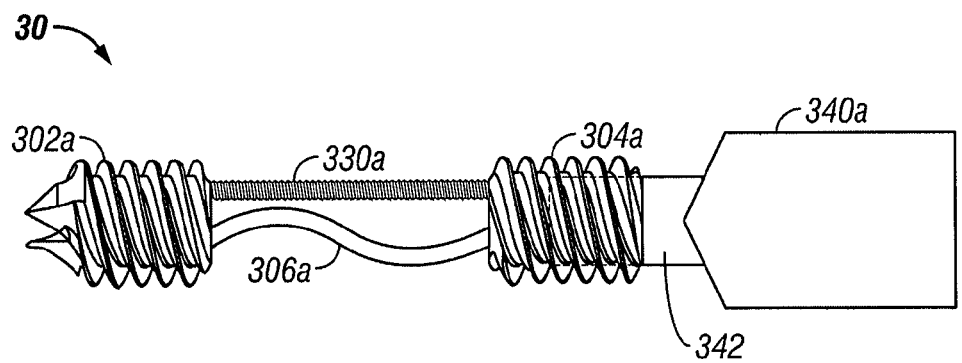
FIG. 5A is a side view of a compression device according to an alternative embodiment of the invention, shown with a spacer comprising a driver instrument.
Figure 5B:
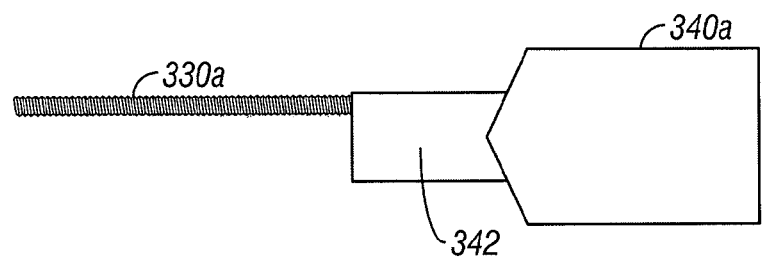
FIG. 5B shows the driver instrument of the device of FIG. 5A, shown with a driver instrument.
Figure 5C:
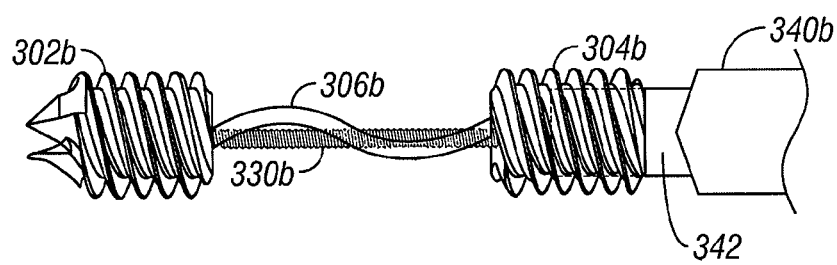
FIG. 5C is a side view of a compression device according to yet another embodiment.

With reference now to FIGS. 5A-5B, a screw 30 may include a threaded leading orthopedic structure 302(*a*) and a threaded trailing orthopedic structure 304(*b*), with a spring 306(*a*) disposed between the two. In the illustrated embodiment the spring 306(*a*) is aligned approximately along a central axis of the screw 30 and comprises S-curves to minimize the spring profile. In other embodiments the spring may be a coil. The spring 306(*c*) and the trailing orthopedic structure 304(*b*) may each be provided with one or more holes or longitudinally extending channels to facilitate the insertion of a guide wire and/or spacer member 330(*a*) coupled to a driver instrument 340(*a*). The driver instrument 340(*a*) and spacer member 330(*a*) are illustrated separately in FIG. 5B. The driver instrument 340(*a*) may comprise a larger profile engagement member 342 for coupling to and driving the trailing orthopedic structure 304(*a*). The engagement member 342 may engage the trailing orthopedic structure 304(*b*) using any suitable reversible coupling means including threading or an expanding ring. The spacer member 330(*a*) may have a smaller profile and serve multiple functions including holding the leading 302(*a*) and trailing 304(*a*) orthopedic structures apart (e.g., under the compressive force of the spring 306(*a*)), driving the leading orthopedic structure 302(*a*) into bone, and providing bending resistance to prevent bending of the leading 302(*a*) and trailing 304(*a*) orthopedic structures away from the central axis. In the embodiment illustrated in FIG. 5A, the spacer member 330(*a*) may be disposed along an axis offset from the central axis of the device 30 so as to not interfere with the centrally located spring 306(*a*). Alternatively, as illustrated in FIG. 5C, a spacer member 330(*b*) may be centrally located between leading and trailing members 302(*b*), 304(*b*) to minimize the profile. In this embodiment, the spring 306(*a*) may be configured to wrap around the spacer member 330(*b*) or holes may be provided in the spring 306(*a*) to receive the spacer member 330(*b*).

One embodiment includes a surgical method for inserting a screw 30 according to FIGS. 5A-5B. In this embodiment, the screw 30 is coupled to the driver instrument 340(*a*) by inserting the spacer member 330(*a*) through a hole in the trailing orthopedic structure 304(*b*) and into a receptacle in the leading orthopedic structure 304(*b*). The spring 306(*a*) is then tensioned by engaging the trailing orthopedic structure 304(*b*) with the engagement member 342. The screw may then be inserted into pre-positioned bone fragments using the driver instrument 340(*a*). The engagement member 342 is then decoupled from the trailing orthopedic structure 304(*b*) such that the spring 306(*a*) can apply a compressive force between the orthopedic structures 304(*a*), 304(*b*).

Figures 6, 7:
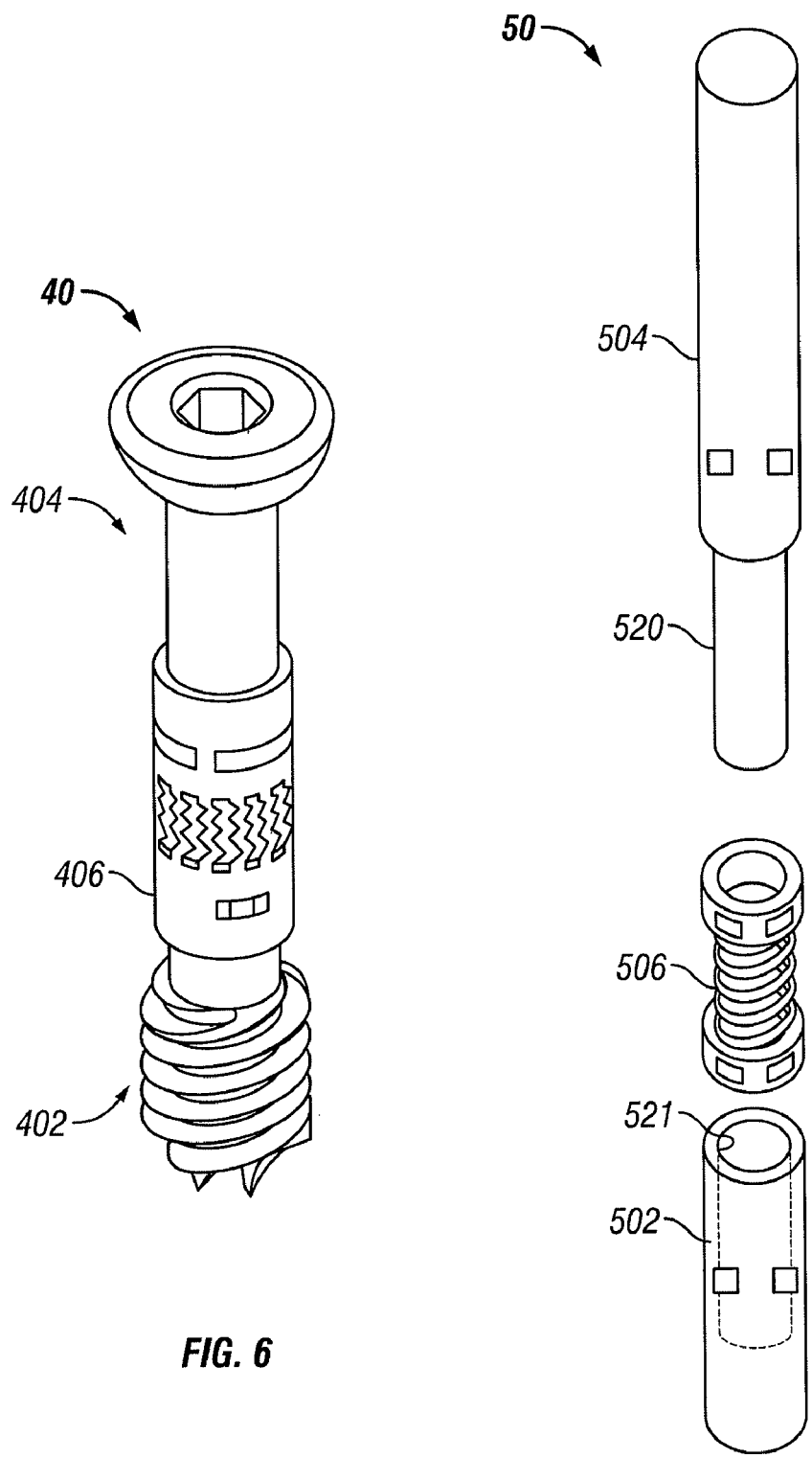
FIG. 6 is a perspective view of a compression device according to a further embodiment.
FIG. 7 is a perspective view of a compression device according to a still further embodiment.

Additional generally cylindrical embodiments are illustrated in FIGS. 6 and 7. FIG. 6 shows a screw 40 having a partially threaded leading orthopedic structure 402 and a blunt headed trailing orthopedic structure 404, with a spring 406 disposed between the two. The blunt orthopedic structure 404 may be configured to engage bone or a plating system. The blunt orthopedic structure 404 may further include a polyaxial screw head, a fixed angle feature, and/or a locking mechanism configured to engage with and secure a plating system. The leading and trailing sections 402, 404 can be held apart or separated by any suitable mechanism, such as the interengaging structures described in connection with FIGS. 1-3, or by a spacer member similar to those described in connection with FIGS. 5A-5C. The screw 40 may be inserted using methods similar to those described for the screw of FIGS. 103.

FIG. 7 shows a device 50 having a leading orthopedic structure 502, a trailing orthopedic structure 504, and a spring 506 disposed between the two. Each of the leading and trailing orthopedic structures 502, 504 comprises an unthreaded rod. The leading orthopedic structure 502 may include a aperture 521 configured to closely receive a male portion 520 of the trailing orthopedic structure 504 to provide bending resistance. The male and female portions 520, 521 may be configured to allow or restrict axial rotation, depending on their cross-sectional shape. The spring member 506 can be controlled by a driver instrument (see FIGS. 5A, 5B) used in combination with a spacer (see FIGS. 5A, 5B) or internal mechanism (see FIGS. 3A, 3B). The illustrated embodiment can be used, for example, in spine fusions, in which rods are attached to other devices in the spine. The spring member 506 can be oriented to apply either compression or tension (e.g., by using either a compression or tension spring 506) to the surrounding bone through the device 50 upon removal or absorption of a spacer (or upon full engagement of an interengaging mechanism). Alternatively one of the leading and trailing sections 502, 504 could be compressed and the other distracted to create a bending moment applied to the spine. The illustrated embodiment can also be used with intramedullary rods to facilitate healing of fractures or lengthening of bone as described in more detail below.

With reference now to FIGS. 8A-8D, various devices 60(a)-60(b) are illustrated which include one or more springs 606 disposed between two plate orthopedic structures 602, 604. The plate orthopedic structures 602, 604 may each include at least one screw hole 605. Each plate orthopedic structures 602, 604 may be anatomically shaped to fit specific bones. The springs 606 may be disposed in parallel to each other or oriented in differing directions to connect additional plate orthopedic structures. For a spinal application, for example, a device can include multiple points of curvature to fit the spine profile. For a clavical application, a device can follow the S-shaped curves of the clavicle. For long bones or fingers, one or more plate sections can be elongated. For ankles and wrists, multiple plates and springs can be used which mimic the complex shape and orientation of carpal, tarsal, metacarpal, and metatarpal bones.

Figure 8A:
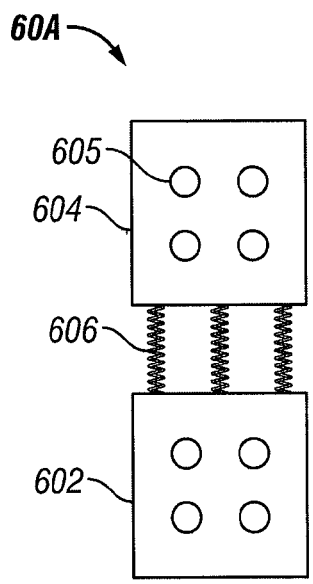
FIGS. 8A-8D show top plan views of compression devices according to various embodiments.
Figure 8B:
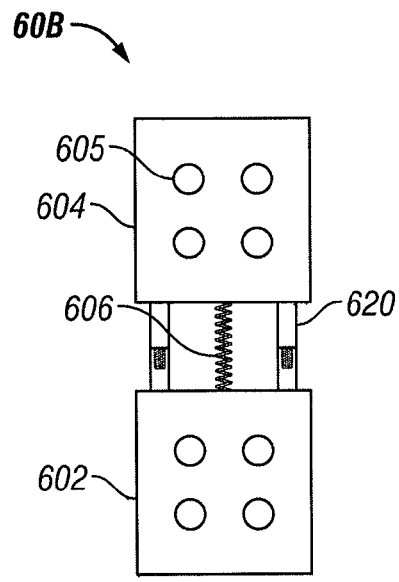

FIG. 8B shows an embodiment in which the plate orthopedic structures 602, 604 are separated by a spring member 606 and connected by a sliding members 620 which may restrict bending but allow axial translation. The sliding member 620 can be a male and female coupling, tongue in groove, dovetail, or other semi-constrained mechanism.

Figure 8C:
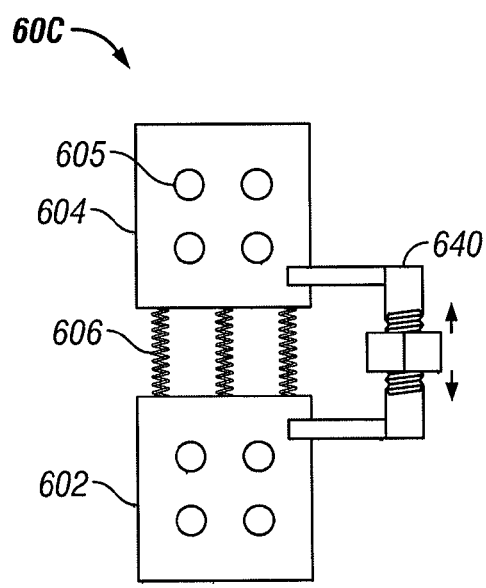

FIG. 8C shows the plate sections 602, 604 separated by an spacer 640. The spacer 640 can be static or adjustable to allow for exact spacing of the plate sections 602, 604. The spacer 640 can be coupled to holes, slots, or posts on the plate orthopedic structures 602, 604, or can be inserted between the plate orthopedic structures 602, 604. After attachment of the device 60(c) to bone, the spacer 640 can be removed to allow application of compression or tension by the spring member 606 through the plates 602, 604.

Figure 8D:
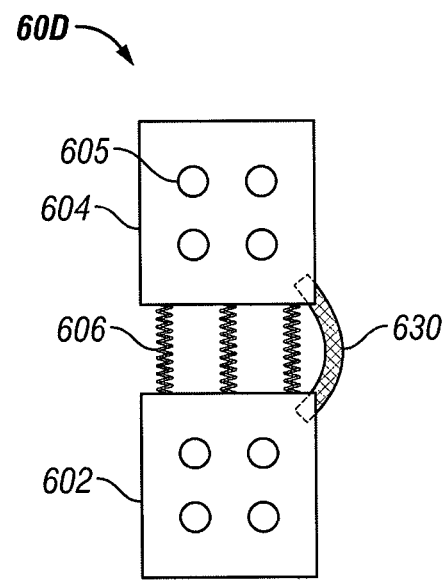

FIG. 8D shows the plate orthopedic structures 602, 604 held apart by at least one temporary spacer 630. The spacer can be removed during implantation of the device 60(d), or can be made from an absorbable or degradable biocompatible material so that it degrades in vivo during healing. As illustrated in the figure, the spacer 630 can be temporarily maintained in position with cuts or other features provided in the plates 602, 604. In one embodiment a spacer 630 is fixed to the plates 602, 604. In another embodiment, spacers of varying dimensions can be exchanged before or during an operation, to increase or decrease the amount compression or extension across the device. A spacer 630 can be designed with specific desirable absorption rate based on variables such as patient age, weight, or fracture severity. An absorbable spacer 630 may, for example, be configured to transfer loads to bone after approximately 4-8 weeks. Such a configuration may be desirable for a younger patient with a simple fracture. Alternatively, an absorbable spacer 630 may be configured to transfer loads after approximately 3-5 months in the body. Such a configuration may be desirable for an older patient with a comminuted fracture. Other embodiments can be configured for additional timing options.

Some embodiments include a surgical method for inserting the devices 60(a)-60(b). For example, after pre-positioning bones or bone fragments in the desired configuration, a surgeon may place one of the devices 60(a)-60(b) onto the surface of the bones or bone fragments. During insertion, the devices 60(a)-60(b) may be held apart by spacer 630, 640. In the case of an adjustable spacer 640, the surgeon may then adjust the spacing between the plates 602, 604 so that they are aligned in the desired positions on the bones or bone fragments. After positioning the devices 60(a)-60(b), the surgeon may then drive bone screws or nails through screw holes 605 to secure the plates 602, 604 to the bone surface. The spacer 630, 640 may then be optionally removed.

With reference now to FIGS. 9A-9B, a device 70 includes multiple plates 704(a), 704(b), 704(c) connected to a central plate 702 by springs 706(a), 706(b), 706(c), respectively. As mentioned above in connection with FIGS. 8A-8D, the springs 706 and/or the plates 702, 704 can be configured to bend, deflect, contract, or expand in one or more directions. One or more of the plates 702, 704 can be temporarily held apart or restrained with a spacer which is removed intraoperatively or made from a biocompatible, absorbable or degradable material. FIG. 9B illustrates a spacing instrument 730 having multiple prongs or attachments 732, which may be static or adjustable for different sizes or amounts of compression (or tension) in the device 70. The spacing instrument 730 may be used to hold the plates 702, 704 apart as well as facilitate insertion of the device 70. In some embodiments, the prongs 732 may be adjustable to adjust the various spacings between the plates 704(a), 704(b), 704(c) and the central plate 702. A portion of an alternative embodiment is illustrated in FIG. 10, which shows the central plate 702 connected to a plate 704(d) by a spring 706(d). The embodiment may include one or more sliding members 740 configured to resist bending between the plates 702, 704(d). Bending resistance can also be provided by the configuration of the spring 706(d).

One embodiment includes a surgical method for inserting the device 70. After positioning bones or bone fragments in the desired locations, a surgeon may couple the plates 704(a), 704(b), 704(c) to the prongs 732 on the spacing instrument 730. In some embodiments, the spacings may be adjusted by adjusting the prongs 732. Next, the spacing instrument 730 is used to position the device 70 in the desired location on the surfaces of the bones or bone fragments. Then, bone screws or nails are used to attache the bone plates 704(a), 704(b), 704(c), 702 to the bones or bone fragments. Finally, the spacing instrument 730 is decoupled from the device 70, causing the springs 706 to supply compressive or tensile forces to the bones or bone fragments.

Figure 11A:
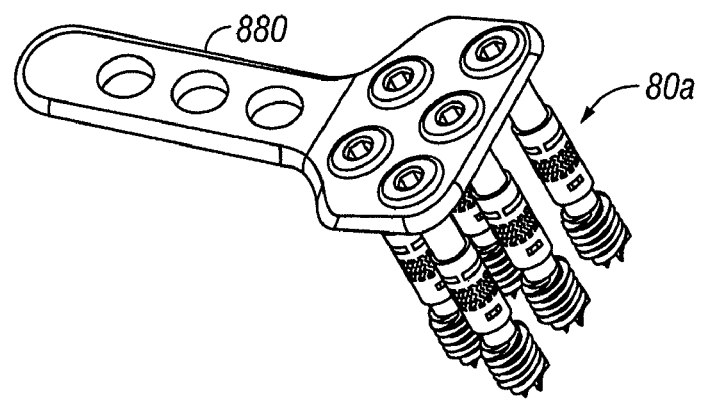
FIG. 11A illustrates the use of several compression devices with a standard plating system.
Figure 11B:
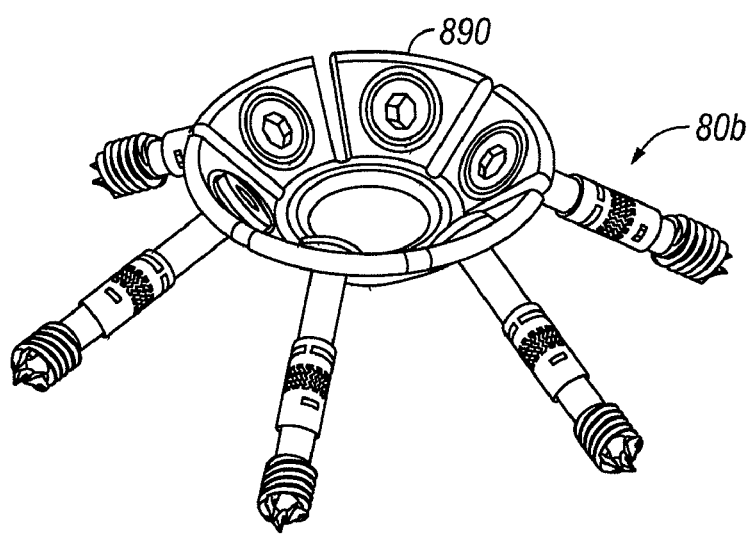
FIG. 11B illustrates the use of several compression devices with another plating system.

FIGS. 11A and 11B illustrate the use of several active compression screws 80(a) and 80(b) in various configurations and with standard plating systems 880, 890, respectively. The active compression screws 80(a) and 80(b) may be as described in FIGS. 1-3 or 6 or any other suitable design. By using active compression screws 80(a) and 80(b) as described herein, the plating systems 880, 809 may be held against bone during the healing process without loosening of the attachment screws.

Figure 12:
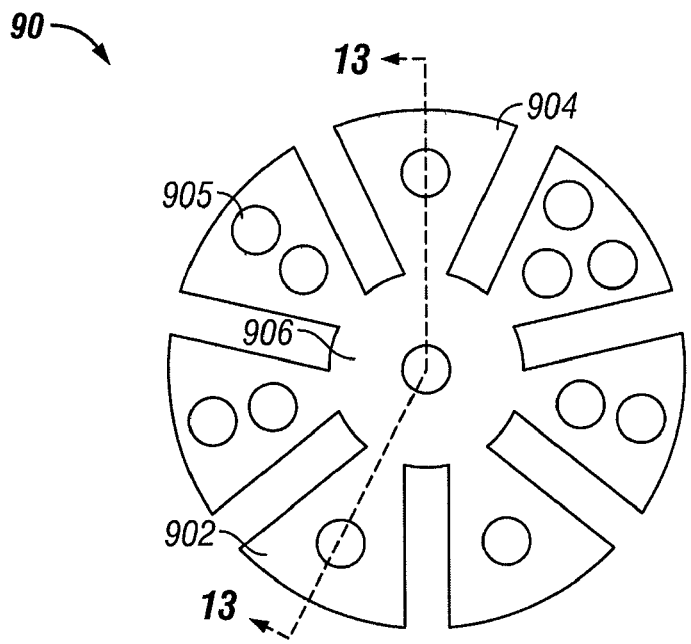
FIG. 12 is a top plan view of multi-fragment compression device according to an embodiment.
Figure 13A:
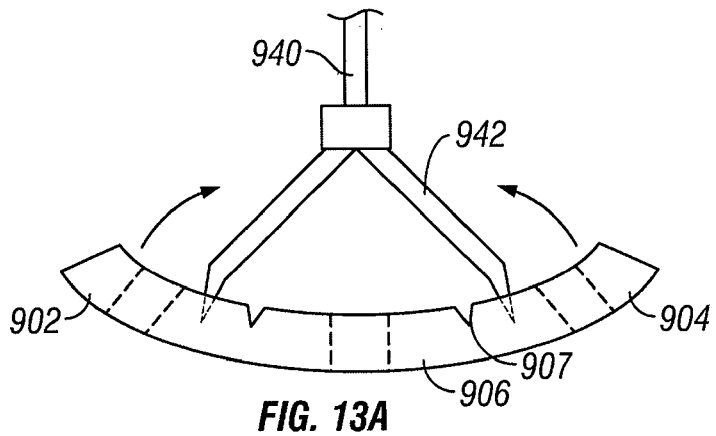
FIG. 13A is a cross-sectional view of the device of FIG. 13A taken along line 13-13 illustrating its use with a spacer, the spacer comprising a restraining instrument.
Figure 13B:
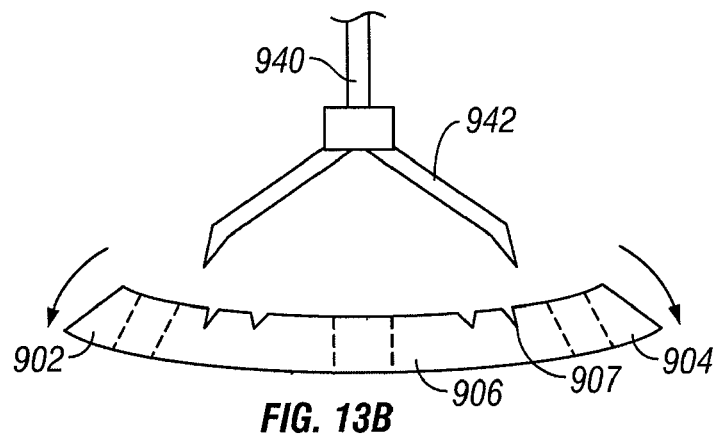
FIG. 13B is a cross-sectional view of the device of FIG. 13A taken along line 13-13 illustrating its shape after removal of the spacer.

FIGS. 12 and 13A-13B illustrate a device 90 having orthopedic plates 902, 904 formed integrally with spring 906. In this embodiment, the spring 906 takes the form of a bendable portion of the plates 902, 904. The plates 902, 904 and/or the spring 906 may be provided with at least one screw hole 905 for fixing the device 90 to bone. The device 90 (including the plates 902, 904 and the spring 906) may be curved or otherwise configured to be recessed at least partially below the bone surface. For example, prior to attachment, a surgeon may remove a portion of bone to create a hollow to receive the plates 902, 904. As illustrated in FIG. 13A, the curvature of the device 90 may be restrained against the bending force of the spring 906 using a restraining instrument 940 that comprises a spacer 942. The spacer 942 may comprise prongs that can engage with at least one notch or thin section 907 in the device 90. In some embodiments, the prongs of the spacer 942 may be adjustable to adjust the extent of the bending of the plates 902, 904. FIG. 13B shows the changed shape of the device after removal of the spacer 942. The device 90 may, for example, comprise a four-corner carpal fusion plate, and may be used to rotate and/or apply compression to carpal bones or bone fragments. The device 90 may be inserted use a surgical method similar to that described with respect to FIGS. 9A-9B.

Still further embodiments are illustrated in FIGS. 14A and 14B. FIG. 14A shows a intermedullary nail 45 having a leading rod 452 comprising the distal aspect of the intramedullary nail 45 and a trailing rod 454 comprising the proximal aspect of the intramedullary nail 45. The leading and trailing rods 452, 454 can be shaped to fit specific anatomic geometries, and may be provided with one or more holes for securing the nail 45 to bone with screws or pins. The leading and trailing rods 452, 454 can be connected by a male support member 470 on the trailing rod 454 which fits into a female portion 471 of the leading rod 452. The male/female coupling may be configured to restrict bending between the rods 452, 454 while allowing axial translation of either or both of the sections 452, 454. In addition, if a non-circular cross section is used, the male/female coupling may be configured to restrict axial rotation. For example, the male support member 470 may have an elliptical, hexagonal or otherwise non-circular cross section. The support member 470 and female portion 471 can be provided with one or more interengaging mechanisms, such as a retaining pin or screw 466 and corresponding hole 467. The hole 467 may comprise a slot or other configuration to maintain an initial position for ease of application during surgery but allow axial compression during bone healing. A compression spring 456 may be disposed between the leading and trailing sections 452, 454. The spring 456 may be configured to transfer 100% of light loads (such as those created by standing) to the bone, but only gradually allows heavier bone loading during walking or exercising as part of a recovery program. Similar to the embodiments described earlier, a temporary spacer may be employed between the leading 452 and trailing 454 rods during insertion of the intermeduallary nail 45 into the bone marrow canal to maintain and initial desired spacing. After insertion, the spacer may be removed to allow compression between the leading 452 and trailing 454 rods.

Figure 15:
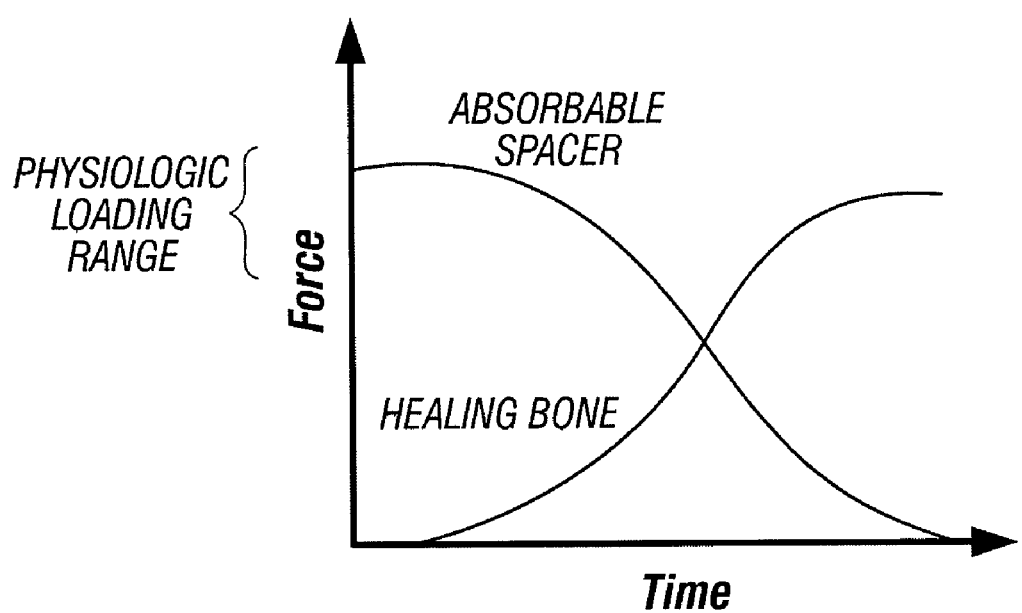
FIG. 15 is a line graph illustrating the relationship between increasing force across healing bone and decreasing force across a spacer in the device of FIG. 14B as the spacer absorbs.

FIG. 14B shows an embodiment in which compression may be facilitated by body weight or muscle forces instead of using a compression spring. The device 55 includes leading and trailing sections 552, 554 separated by a temporary spacer 556. The spacer can be removed intra-operatively or be made from an absorbable material to gradually transfer forces to the healing bone. The spacer 556 can be formed from any suitable biocompatible material, such as ceramic or PLLA or PEG polymer. The spacer 556 can be maintained in position by fitting into grooves or holes provided in the leading and/or trailing sections 552, 554. The spacer 556 can be rigidly attached to the orthopedic devices or designed to be placed, exchanged, and/or removed either pre-operatively or intra-operatively. The spacer can have configured with varying absorption times, depending on the requirements of the particular application and based on several variables such as patient age, weight, or severity of fracture. FIG. 15 shows a graph illustrating a force distribution between an absorbable spacer and healing bone. As illustrated in the graph, as the absorbable spacer disintegrates over time, compressive forces due to physiologic loading is progressively transferred more to the bone than the intermedullary nail.

In some embodiments, a non-bioabsorbable spacer is provided. In these embodiments, spacers may be interchanged as desired over time to provide varying spacing distances and thereby varying the distribution of physiologic loading forces between the intermeduallary nail and the healing bone. In some embodiments, a kit is provided comprising multiple spacers of varying sizes. In other embodiments, a kit is provided comprising both absorbable and non-absorbable spacers, providing flexibility to the surgeon.

Figure 16A:
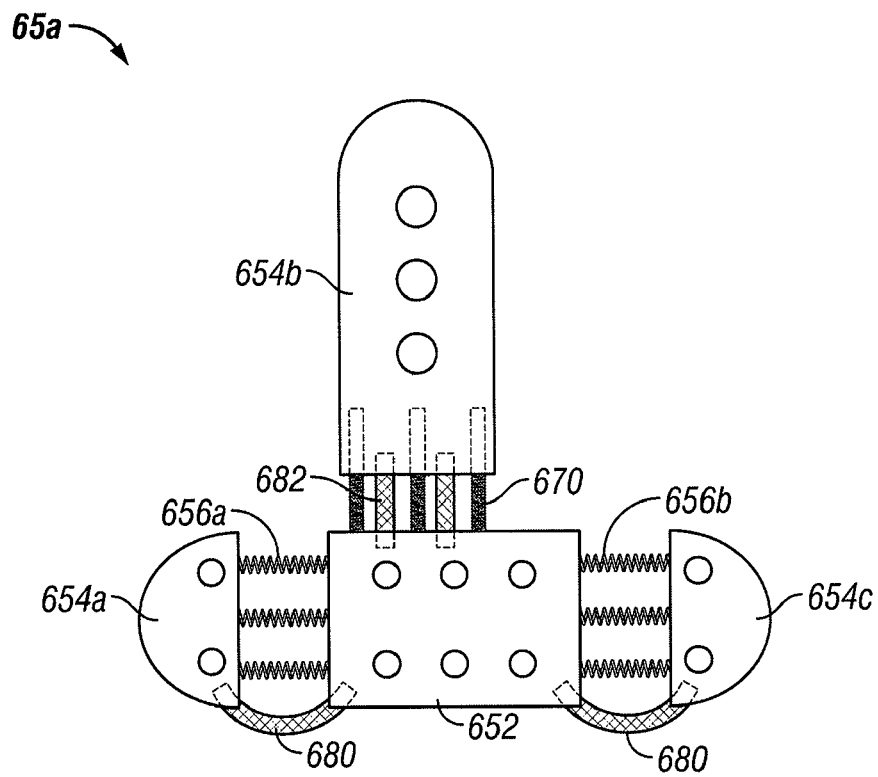
FIGS. 16A and 16B show multi-plate compression devices according to further embodiments of the invention.
Figure 16B:
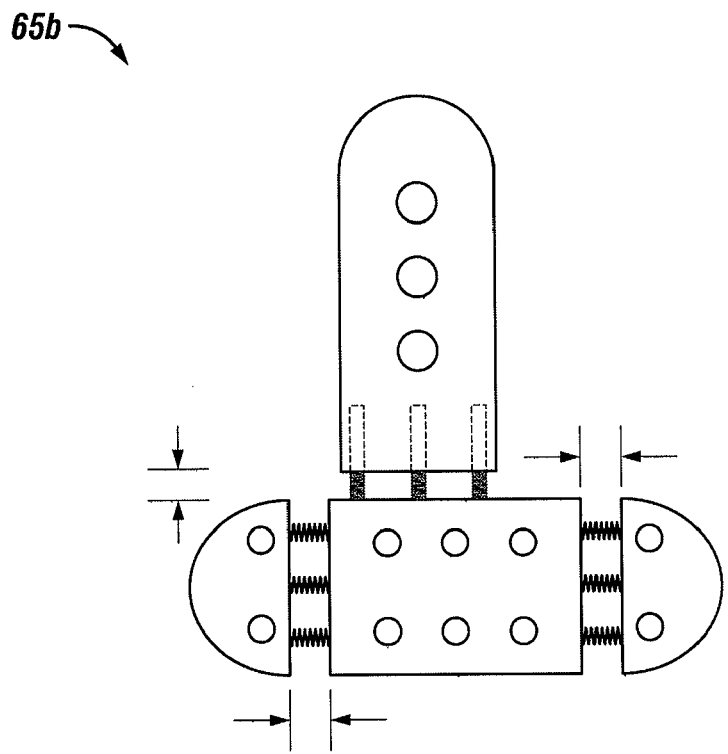

As illustrated in FIGS. 16A, 16B, embodiments of the invention can incorporate multiple aspects of the inventive technology. As shown in FIG. 16A, for example, a device 65(a) can include multiple plates 652, 654(a)-(c) having varying configurations. The plates 652, 654 may be connected by multiple springs 656(a), 656(b) of varying configurations. Bending resistance members 670 may also be employed between plates 652, 654. The bending resistance members 670 may comprise a sliding mechanism which allows bone compression from body weight or muscle forces. The plates may further be held apart (or pulled together) by one or more absorbable or non-absorbable spacers 680, 682. As illustrated in FIG. 16B, the springs 656(a), 656(b) can apply increasing compression to bone as the spacers 680, 682 degrade and as bone heals. The springs 656(a), 656(b) can be formed to apply compression in one or more directions by having at least one radius of curvature in a different plane than the primary spring direction.

Some embodiments of the invention include surgical methods of attaching bone to bone. In some embodiments, the method may include attaching a first orthopedic structure to a first piece of bone and attaching a second orthopedic structure to a second piece of bone. Where the orthopedic structure comprises a plate, for example, the structure may be attached to bone using screws or nails inserted through one or more holes provided in the plate. Where the orthopedic structure comprises a screw or other threaded device, the structure may be attached by inserting the threaded device directly into bone. A spring may be disposed between the orthopedic structures. During insertion, the structures may be pulled together or held apart by a spacer. Depending on the application, the spacer may be configured to place the spring in either a neutral or a compressed state. The spacer may also be used to hold the structures in a particular configuration with respect to one another, in order to facilitate implantation of the structures through a small surgical opening. The surgeon may choose between spacers of varying sizes in order to appropriately position the structures with respect to the bones or bone fragments. Alternatively, in the case of an adjustable spacer, the surgeon may appropriately position the structures by adjusting the spacer itself. A spacer may also comprise a manually operated restraining tool or driver instrument. Where a spacer comprises a non-absorbable spacer or restraining instrument, the surgeon may then remove the spacer to allow the spring to apply tension or compression (through the orthopedic structures) to the surrounding bone. Should the surgeon determine that permanent restriction of compression or tension is desirable, a non-absorbable spacer may optionally be left in the surgery site between the structures. Should the surgeon determine that compression or tension is desirably delayed, an absorbable spacer may used.

Further embodiments include surgical kits comprising one or more of the devices described herein. For example, kits may include a selection of absorbable and non-absorbable spacers of varying sizes and/or absorption rates. Kits may further include a selection of restraining instruments or tools. In some embodiments, the kit may include surgical tools useful for inserting the devices. For example, kits may be provided comprising one or more active compression or tension screw or plate system as described above as well as inserter instruments useful for inserting the screws and/or plate systems.

It will be understood by those of skill in the art that numerous and various modifications can be made without departing from the spirit of the present invention. Therefore, it should be clearly understood that the forms of the invention described herein are illustrative only and are not intended to limit the scope of the invention.

What is claimed is:

1. A bone fixation device comprising:
   a first orthopedic structure configured to engage bone;
   a second orthopedic structure configured to engage bone;
   a spring disposed between the first and second orthopedic structures; and
   a first portion integral with the first orthopedic structure and a second portion integral with the second orthopedic structure;
   wherein the first and second orthopedic structures are aligned along a longitudinal axis and the first portion and the second portion are configured to have at least two rotational orientations relative to each other, wherein in a first rotational orientation, an end surface of an end structure of the first portion contacts an end surface of an end structure of the second portion to hold the first and second orthopedic structures apart against a first force of the spring, and wherein in a second rotational orientation, different from the first rotational orientation, the first and second portions are oriented such that the first and second orthopedic structures can move axially relative to each other in response to a second force of the spring less than or equal to the first force in order to urge the first and second orthopedic structures together.

2. The device of claim 1, wherein the first and second orthopedic structures are independently selected from the group consisting of a bone screw, a bone nail, a head member, a bone plate, a rod, a proximal portion of an intramedullary nail, and a distal portion of an intramedullary nail.

3. The device of claim 1, wherein the spring is formed separately from the first and second orthopedic structures.

4. The device of claim 1, wherein when the first and second orthopedic structures are in the first rotational orientation, the first portion contacts the second portion in such a manner that torque sufficient to drive the device into bone can be transmitted from one of the orthopedic structures to the other orthopedic structure.

5. The device of claim 1, wherein when the first and second orthopedic structures are in the second rotational orientation, the first portion contacts the second portion in such a manner that torque sufficient to withdraw the device from bone can be transmitted from one of the orthopedic structures to the other orthopedic structure.

6. The device of claim 1, wherein the first portion comprises a protrusion and wherein the second portion comprises an aperture configured to receive the protrusion.

7. The device of claim 1, wherein the first orthopedic structure and the second orthopedic structure comprise matched threads such that the device can be screwed into bone in a same manner as a single bone screw.

8. The device of claim 1, wherein the spring comprises material selected from one or more of a shape memory material, stainless steel, and elastic biocompatible material.

9. The device of claim 1, wherein the spring comprises a shape memory alloy.

10. The device of claim 1, wherein the spring is a coil spring.

11. The device of claim 1, wherein the spring is a compression spring.

12. The device of claim 1, wherein the spring is a tension spring.

13. The device of claim 1, wherein the device further comprises a bending resistance member contacting the first and second orthopedic structures, wherein the first and second orthopedic structures are aligned along a common axis and wherein the bending resistance member is configured to restrict bending of either orthopedic structure away from an axis of the device.

14. The device of claim 13, wherein one of the orthopedic devices comprises an aperture and the bending resistance member comprises a protrusion configured to be slidingly received by the aperture.

15. The device of claim 14, wherein the aperture and protrusion each have a circular cross section.

16. The device of claim 13, wherein one of the orthopedic devices comprises a groove and the bending resistance member comprises a tongue configured to be slidingly received by the groove.

17. A kit comprising the bone fixation device of claim 1, the kit further comprising an inserter configured to insert the bone fixation device into bone.

18. An active compression orthopedic screw comprising:
   a first shaft member positioned at a distal end of said screw;
   a second shaft member positioned at a proximal end of said screw;
   a first portion integral with the first shaft member and a second portion integral with the second shaft member; and
   an elastic member having a first end and a second end;
   wherein said first end of said elastic member is coupled to said first shaft member and said second end of said elastic member is coupled to said second shaft member, and wherein said elastic member is configured to exert a force drawing said first and second shaft members together;
   wherein the first and second shaft members are aligned along a longitudinal axis and the first portion and the second portion are configured to have at least two rotational orientations relative to each other, wherein in a first rotational orientation, an end surface of an end structure of the first portion contacts an end surface of an end structure of the second portion to hold the first and second shaft members apart against a first force of the elastic member, and wherein in a second rotational orientation, different from the first rotational orientation, the first and second portions are oriented such that the first and second shaft members can move axially relative to each other in response to a second force of the elastic member less than or equal to the first force in order to urge the first and second shaft members together.

19. The screw of claim 18, comprising:
   wherein the end structure of the first portion comprises a protrusion extending from the first portion; and
   wherein the end structure of the second portion comprises a protrusion receiving orifice formed in the second portion;
   wherein said protrusion receiving orifice is configured to slideably receive said protrusion.

20. The screw of claim 18, further comprising threads disposed on an outer surface of said first shaft member.

21. The screw of claim 20, wherein said threads comprise self-tapping threads.

22. The screw of claim 18, wherein said elastic member comprises a shape memory alloy.

23. The screw of claim 22, wherein said shape memory alloy comprises Nitinol.

24. The screw of claim 18, further comprising:
at least one blocking member protruding from said second shaft member;
a blocking member receiving recess formed in said first shaft member; and
a rotation stop member protruding from said first member;
wherein said blocking member is configured to maintain a tension in said elastic member and engage said rotation stop when said second shaft member is rotated in a first direction; and
wherein said blocking member is configured to release said tension in said elastic member and enter said blocking member receiving recess when said second shaft member is rotated in a second direction.

25. The screw of claim 18, further comprising:
at least one blocking member protruding from said second shaft member; a blocking member receiving recess formed in said first shaft member;
a rotation stop member protruding from said first member;
wherein said blocking member is configured to maintain a tension in said elastic member and engage said rotation stop member when said second shaft member is rotated in a first direction; and
wherein said blocking member is configured to release said tension in said elastic member and enter said blocking member receiving recess when said second shaft member is rotated in a second direction.

26. A system for coupling a first bone segment to a second bone segment, the system comprising:
a first shaft member positioned at a distal end of a screw;
a second shaft member positioned at a proximal end of said screw, said second shaft member including a bone coupling protrusion;
a first portion integral with the first shaft member and a second portion integral with the second shaft member; and
an elastic member having a first end and a second end;
wherein said first end of said elastic member is coupled to said first shaft member and said second end of said elastic member is coupled to said second shaft member, and wherein said elastic member is configured to exert a force drawing said first and second shaft members together; and
wherein the first and second shaft members are aligned along a longitudinal axis and the first portion and the second portion are configured to have at least two rotational orientations relative to each other, wherein in a first rotational orientation, an end surface of an end structure of the first portion contacts an end surface of an end structure of the second portion to hold the first and second shaft members apart against a first force of the elastic member, and wherein in a second rotational orientation, different from the first rotational orientation, the first and second portions are oriented such that the first and second shaft members can move axially relative to each other in response to a second force of the elastic member less than or equal to the first force in order to urge the first and second shaft members together.

27. The system of claim 26, wherein said first portion- and said second portion are slideably coupled.

28. The system of claim 27,
wherein the end structure of the first portion comprises a protrusion extending from said first shaft member; and
wherein the end structure of the second portion comprises a protrusion receiving orifice formed in;
said protrusion receiving orifice being configured to slideably receive said protrusion.

29. The system of claim 26, wherein said elastic member comprises a shape memory alloy.

30. The system of claim 29, wherein said shape memory alloy comprises Nitinol.

31. An active compression orthopedic screw comprising:
a first shaft member positioned at a distal end of said screw having threads disposed on an outer surface, the first shaft member having an integral first portion;
a second shaft member positioned at a proximal end of said screw, the second shaft member having an integral second portion;
a protrusion extending from said first shaft member;
a protrusion receiving orifice formed in one of said second shaft member, said protrusion receiving orifice being configured to slideably receive said protrusion; and
a shape memory alloy elastic member having a first and a second end;
wherein said first end of said elastic member is coupled to said first shaft member and said second end of said elastic member is coupled to said second shaft member, and wherein said elastic member is configured to exert a force drawing said first and second shaft members together;
wherein the first and second shaft members are aligned along a longitudinal axis and the first portion and the second portion are configured to have at least two rotational orientations relative to each other, wherein in a first rotational orientation, an end surface of an end structure of the first portion contacts an end surface of an end structure of the second portion to hold the first and second shaft members apart against a first force of the elastic member, and wherein in a second rotational orientation, different from the first rotational orientation, the first and second portions are oriented such that the first and second shaft members can move axially relative to each other in response to a second force of the elastic member less than or equal to the first force in order to urge the first and second shaft members together.

32. The screw of claim 31, wherein said shape memory alloy comprises Nitinol.

33. The screw of claim 31, wherein said second shaft member comprises a head disposed on a proximal end of said second shaft member.

* * * * *

UNITED STATES PATENT AND TRADEMARK OFFICE
CERTIFICATE OF CORRECTION

Page 1 of 1

PATENT NO.         : 8,048,134 B2
APPLICATION NO.    : 11/697655
DATED              : November 1, 2011
INVENTOR(S)        : Partin It is certified that error appears in the above-identified patent and that said Letters Patent is hereby corrected as shown below:

Column 14, at Claim 19, Line 54: after "The screw of claim 18" Delete "comprising:"

Column 16, at Claim 28, Line 10: after "a protrusion receiving orifice formed in" insert --second shaft member;--

Column 16, at Claim 31, Line 26: after "said protrusion receiving orifice" Delete "being"

Signed and Sealed this
Seventeenth Day of January, 2012

David J. Kappos
*Director of the United States Patent and Trademark Office*